(12) United States Patent
Liu et al.

(10) Patent No.: US 12,377,008 B2
(45) Date of Patent: Aug. 5, 2025

(54) METHOD FOR REAL-TIME ADJUSTMENT OF GAIT TRAINING PARAMETER

(71) Applicant: HIWIN TECHNOLOGIES CORP., Taichung (TW)

(72) Inventors: Chi-Chia Liu, Taichung (TW); Tzu-Ning Yeh, Taichung (TW); Jia-Ming Shiu, Taichung (TW)

(73) Assignee: HIWIN TECHNOLOGIES CORP., Taichung (TW)

( * ) Notice: Subject to any disclaimer, the term of this patent is extended or adjusted under 35 U.S.C. 154(b) by 613 days.

(21) Appl. No.: 17/872,879

(22) Filed: Jul. 25, 2022

(65) Prior Publication Data
US 2024/0024187 A1 Jan. 25, 2024

(51) Int. Cl.
*A61H 1/02* (2006.01)
*G16H 20/30* (2018.01)

(52) U.S. Cl.
CPC ........... *A61H 1/0262* (2013.01); *G16H 20/30* (2018.01); *A61H 2201/5007* (2013.01); *A61H 2201/5061* (2013.01); *A61H 2201/5071* (2013.01); *A61H 2230/605* (2013.01)

(58) Field of Classification Search
CPC .... A61H 1/0237; A61H 1/024; A61H 1/0244; A61H 1/0262; A61H 3/00; A61H 1/02; B25J 9/0006; G16H 20/30
See application file for complete search history.

(56) References Cited

U.S. PATENT DOCUMENTS

| | | | |
|---|---|---|---|
| 8,147,436 B2 | 4/2012 | Agrawal et al. | |
| 10,022,587 B1 * | 7/2018 | Wu | A61H 1/0262 |
| 10,052,252 B2 * | 8/2018 | Lin | A61H 1/0262 |
| 2004/0097330 A1 * | 5/2004 | Edgerton | A61H 1/0262 |
| | | | 482/54 |
| 2006/0293617 A1 | 12/2006 | Einav et al. | |

(Continued)

FOREIGN PATENT DOCUMENTS

| | | | | |
|---|---|---|---|---|
| CN | 110507322 A | | 11/2019 | |
| CN | 113244084 A | * | 8/2021 | ........... A61H 1/0237 |
| JP | 2021-007481 A | | 1/2021 | |

OTHER PUBLICATIONS

English translation for CN 113244084, machine translated by espacenet.com, translated on May 8, 2025.*

*Primary Examiner* — Tu A Vo
(74) *Attorney, Agent, or Firm* — Muncy, Geissler, Olds & Lowe, P.C.

(57) ABSTRACT

A method for real-time adjustment of gait training parameter includes steps: (a) collecting the muscle relaxation gait data of the first user measured during gait training in a muscle relaxation state and the active force output gait data of a first user measured during the gait training in the first user's active force output state, and establishing a standard motion model based on the ratio of the first user's active force output gait data to the first user's muscle relaxation gait data; (b) obtaining the muscle relaxation gait data of a second user in a state of muscle relaxation, and estimating the personalized training model by combining the muscle relaxation gait data of the second user with the standard motion model; (c) determining the second user meets the standard of the personalized training model, then adjusting the personalized training model, and providing an auxiliary training model.

9 Claims, 14 Drawing Sheets

(56) References Cited

U.S. PATENT DOCUMENTS

| | | | |
|---|---|---|---|
| 2007/0282228 A1* | 12/2007 | Einav | A63B 21/00181 600/300 |
| 2008/0234113 A1* | 9/2008 | Einav | A61H 1/0237 482/142 |
| 2008/0255488 A1* | 10/2008 | Agrawal | A63B 69/0064 623/24 |
| 2011/0021957 A1* | 1/2011 | Shinomiya | A61H 1/0262 601/5 |
| 2011/0071442 A1* | 3/2011 | Park | A61B 5/112 601/35 |
| 2013/0338549 A1* | 12/2013 | Korenaga | A63B 23/1209 601/33 |
| 2014/0087922 A1* | 3/2014 | Bayerlein | A63B 21/00181 482/54 |
| 2014/0100491 A1* | 4/2014 | Hu | A61H 3/008 601/23 |
| 2014/0371640 A1* | 12/2014 | Schorgendorfer | A61H 1/0266 601/35 |
| 2015/0297934 A1* | 10/2015 | Agrawal | A61H 1/0266 482/4 |
| 2016/0213972 A1* | 7/2016 | Waldner | A63B 22/0058 |
| 2018/0085276 A1* | 3/2018 | Brodard | A61N 1/0452 |
| 2018/0104542 A1* | 4/2018 | Kwon | A63B 21/0058 |
| 2019/0336379 A1* | 11/2019 | Lin | A61H 1/0266 |
| 2020/0078251 A1* | 3/2020 | Benda | A61H 3/008 |
| 2020/0406097 A1* | 12/2020 | Otsuki | G06V 40/25 |
| 2020/0411196 A1* | 12/2020 | Otsuki | G16H 50/30 |
| 2021/0000677 A1* | 1/2021 | Otsuki | G06V 10/82 |
| 2021/0005105 A1* | 1/2021 | Otsuki | A61H 3/008 |
| 2021/0005106 A1* | 1/2021 | Otsuki | G05B 13/0265 |
| 2021/0060383 A1* | 3/2021 | Huang | A61B 5/4836 |
| 2021/0086027 A1* | 3/2021 | Lin | A61H 1/0237 |
| 2021/0283001 A1* | 9/2021 | Von Zitzewitz | A61H 3/008 |

* cited by examiner

10

Step (a): The sensing unit collects a first user's muscle relaxation gait data measured during gait training in a muscle relaxation state and the first user's active force output gait data measured during the gait training in the first user's active force output state, and then the control unit establishes a standard motion model based on the ratio of the first user's active force output gait data to the first user's muscle relaxation gait data.

Step (b): The control unit obtains a motion model of a second user, which comprises a second user's muscle relaxation gait data measured during the gait training under the muscle relaxation state of the second user. By combining the second user's muscle relaxation gait data with the standard motion model, a personalized training model is estimated.

Step (c): The control unit determines whether the actual training state of the second user conforms to the standard of the personalized training model, and then adjusts the personalized training model and provides an auxiliary training model.

FIG. 1

METHOD FOR REAL-TIME ADJUSTMENT OF GAIT TRAINING PARAMETER

BACKGROUND OF THE INVENTION

1. Field of the Invention

The present invention is related to gait training technology, and particularly refers to a method for real-time adjustment of gait training parameter

2. Description of the Related Art

Generally, in the process of gait training, gait training equipment is usually used to assist users in gait training.

Please refer to a powered orthosis as provided in U.S. Pat. No. 8,147,436. As shown in FIG. 7 in the said patent, it mainly collects the walking data of 6 normal people with active effort as an ideal model of the gait trajectory, and plans the allowable error space of the tunnel type on the periphery of the gait trajectory. This provides users with a training effect close to the ideal model in gait training.

However, as in the above-mentioned U.S. Pat. No. 8,147,436, the technology of applying the ideal model to all users for training does not take into account the individual differences of users to plan the motion model, therefore, the ideal model planned in this patent is difficult to be suitable for different users.

In addition, please refer to an adaptive active training system provided by Chinese Patent No. CN 113244084A. As shown in FIG. 6 in the patent, it mainly includes a sensing module, a control module and a motion module. By recording the physiological signals of each section when the user's muscle strength is relaxed and driven by the exoskeleton, the physiological signal threshold of each section is calculated, and the training difficulty is adjusted in real time according to the user's physiological state signal during training.

However, as in the above-mentioned Chinese Patent No. CN 113244084A, only the user's own gait data is used as a reference, and no reference is made to the gait data of normal people or other users. Therefore, the training model planned in this patent cannot achieve the optimal gait training effect.

SUMMARY OF THE INVENTION

The present invention has been accomplished under the circumstances in view. It is the main object of the present invention to provide a method for real-time adjustment of gait training parameter, which can plan a personalized motion model according to the state of different users, and can recommend suitable training difficulty according to the data of the user's output force during training, so as to achieve the effect of adjusting the training difficulty in real time according to the actual performance during training.

To achieve this and other objects of the present invention, the invention provides a method for real-time adjustment of gait training parameter, which is applicable to a gait training equipment comprising a sensing unit, a training unit and a control unit. The control unit is electrically connected to the sensing unit and the training unit, and controls the operation of the training unit. The method for real-time adjustment of gait training parameter comprises the steps of:

(a) The sensing unit collects the muscle relaxation gait data of at least one first user measured during gait training in a muscle relaxation state and the active force output gait data of the at least one first user measured during the gait training in the first user's active force output state, and then the control unit establishes a standard motion model based on the ratio of the first user's active force output gait data to the first user's muscle relaxation gait data.

(b) The control unit obtains a motion model of a second user, which comprises the muscle relaxation gait data of the second user measured during the gait training under the muscle relaxation state of the second user, then estimate at least one personalized training model by combining the second user's muscle relaxation gait data with the standard motion model.

(c) The control unit determines whether the actual training state of the second user conforms to the standard of the at least one personalized training model, and adjusts the at least one personalized training model and provides an auxiliary training model.

Thereby, the present invention provides a method for real-time adjustment of gait training parameter. According to the state of the second user, a personalized training model belonging to the second user can be planned. In the training, it can recommend suitable auxiliary training models according to the data of the second user's force output, so as to achieve the effect of adjusting the training difficulty in real time according to the actual performance during training.

BRIEF DESCRIPTION OF THE DRAWINGS

FIG. 1 is a flow chart of a preferred embodiment of the present invention.

DETAILED DESCRIPTION OF THE INVENTION

Figure 2:
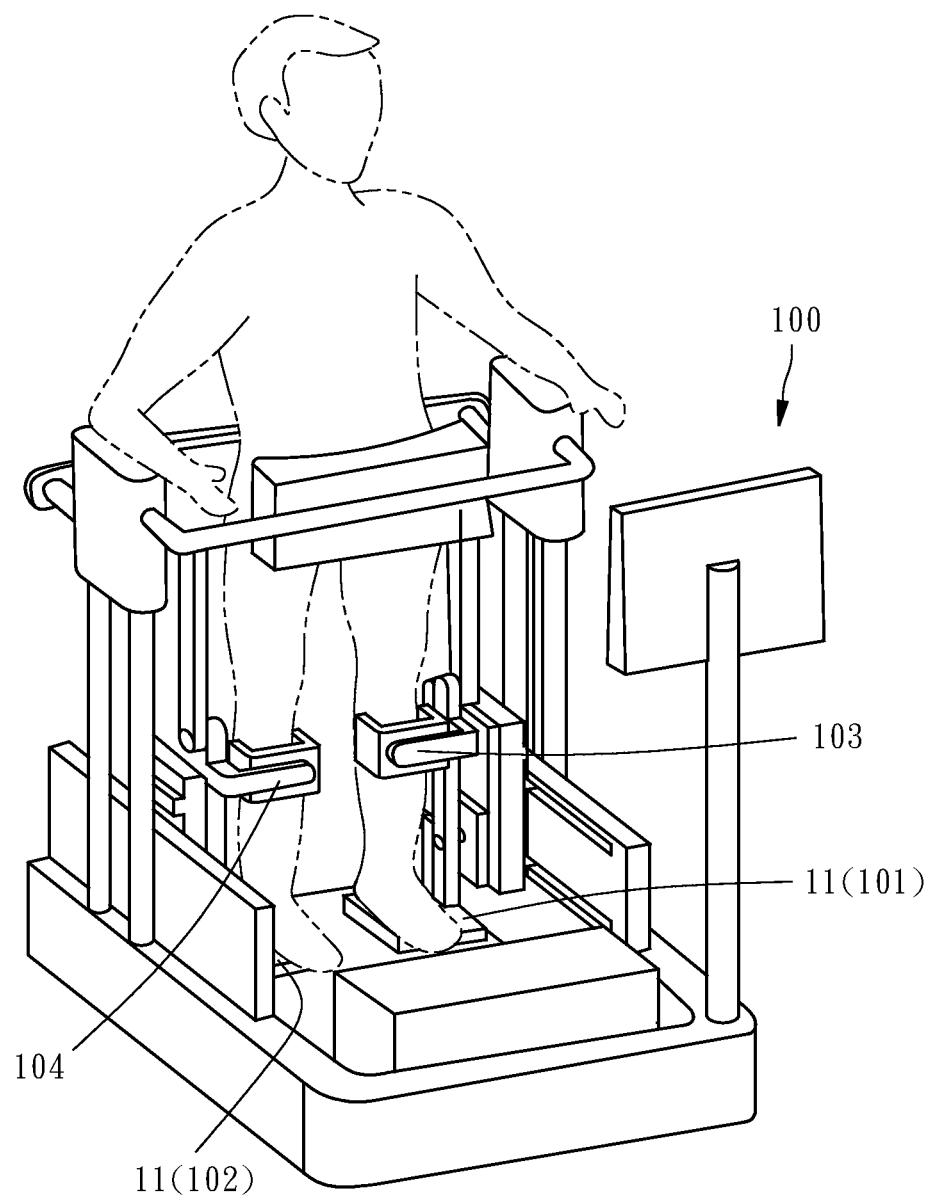
FIG. 2 is a schematic diagram of the use state of a preferred embodiment of the present invention when used with gait training equipment.

In order to describe the technical features of the present invention in detail, the following preferred embodiment is hereby described with the help of the drawings as follows: As shown in FIGS. 1-2, the method for real-time adjustment of gait training parameter 10 of the present invention is mainly used in conjunction with a gait training equipment 100. The gait training equipment 100 mainly comprises a sensing unit, a training unit and a control unit. The sensing unit comprises two sole force sensors and two knee pressure sensors. The sole force sensors are respectively a left foot force sensor 101, a right foot force sensor 102. The knee pressure sensors are respectively a left knee pressure sensor 103 and a right knee pressure sensor 104. The training unit comprises two pedals 11 and other components for driving the user's lower limbs for training. The left foot force sensor 101 is arranged on one of the pedals 11, and the right foot force sensor 102 is arranged on the other pedal 11. The control unit is electrically connected with the sensing unit and the training unit, and controls the operation of the training unit. The control unit has analysis and computing capabilities, and can be, but not limited to, a central processing unit (CPU) or other information processing elements with analysis and computing capabilities. When a first user or a second user uses the gait training equipment 100, the gait training equipment 100 provides the control, calculation and operation required by the method for real-time adjustment of gait training parameter 10. The method for real-time adjustment of gait training parameter 10 mainly comprises steps (a), (b) and (c). In this preferred embodiment, the left foot force sensor 101 and the right foot force sensor 102 are load cells; the left knee pressure sensor 103 and the right knee pressure sensor 104 are film pressure sensors. It is worth mentioning that the user can choose the appropriate sensor according to the actual needs, not limited to this.

Figure 2A:
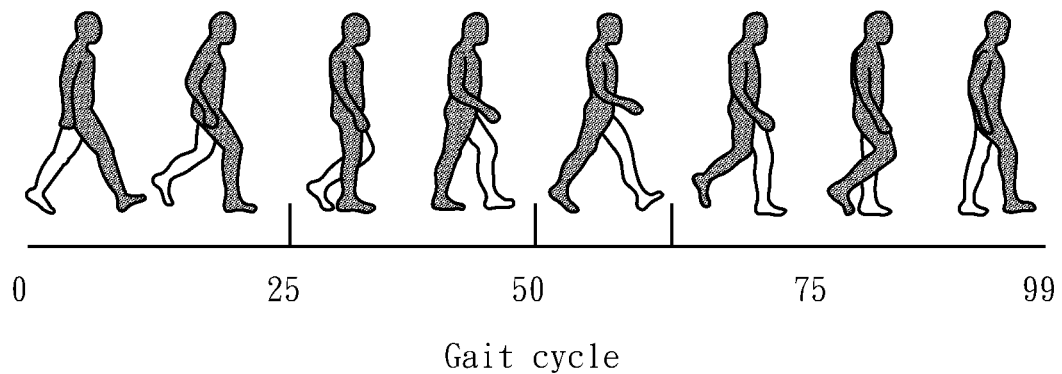
FIG. 2a is a schematic diagram of a preferred embodiment of the present invention showing the gait cycle.

In this preferred embodiment, as shown in FIG. 2a, the gait training comprises at least one gait cycle. The gait cycle corresponds to the gait trajectory of one of the feet. The gait trajectory simulates the process of human walking from the start of the right heel touches the ground to the left toe off the ground, the left heel touches the ground to the right toe off the ground and finally back to the right heel touches the ground. The horizontal axis of FIGS. 2b, 2c, 2d, 2e, 2f, 2g, 3, 3a, 3b, 3c, 3d, 3e corresponds to the gait cycle of FIG. 2a. The data on the graph is divided into 100 equal parts, and the position where the heel of the user's single foot touches the ground corresponds to the starting point of the gait cycle (that is, the data point marked with 0 on the horizontal axis), and the position before the heel of the same foot touches the ground again corresponds to the 99th data point on the horizontal axis.

Figure 2B:
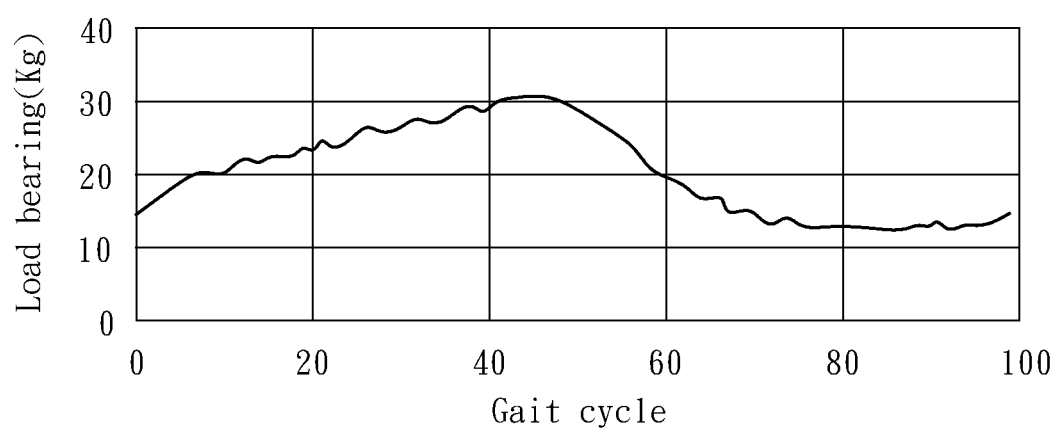
FIG. 2b is a graph of a preferred embodiment of the present invention, showing the muscle relaxation gait data of the first user measured during gait training under the muscle relaxation state of the first user.
Figure 2C:
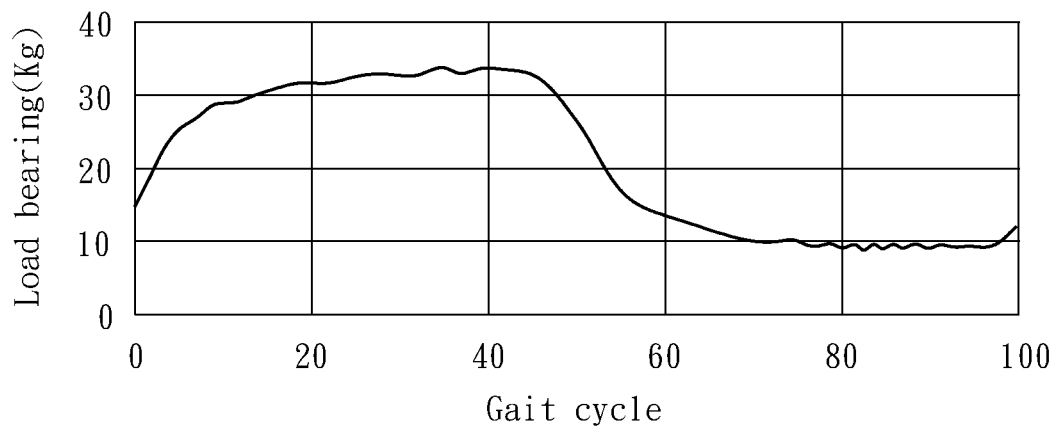
FIG. 2c is a graph of a preferred embodiment of the present invention, showing the first user's active force output gait data measured during gait training in an active force output state.
Figure 2D:
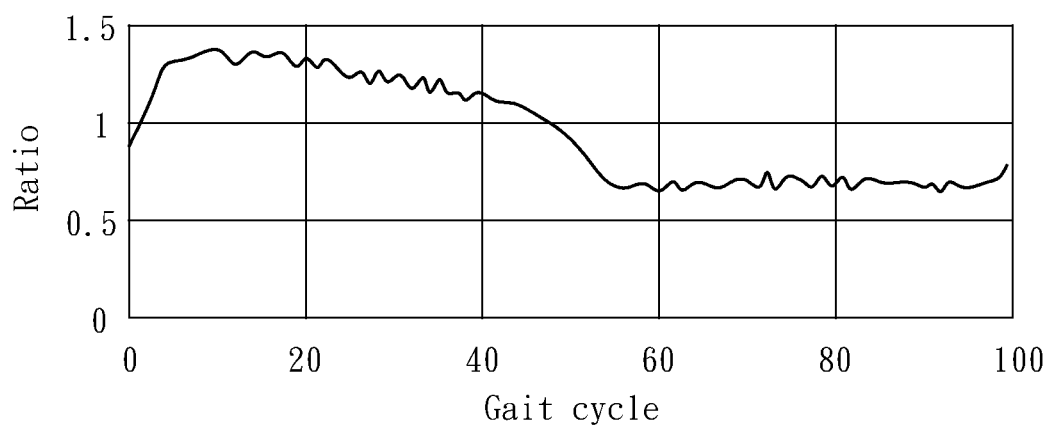
FIG. 2d is a graph of a preferred embodiment of the present invention, showing the ratio of the first user's gait data with active force output and the first user's muscle relaxation gait data.

As shown in FIGS. 1, 2b, 2c, 2d and 2e, in step (a), the sensing unit collects a first user's muscle relaxation gait data measured during gait training in a muscle relaxation state (as shown in FIG. 2b), and the first user's active force output gait data measured during the gait training in the first user's active force output state (as shown in FIG. 2c), the control unit establishes a standard motion model based on the ratio of the first user's active force output gait data to the first user's muscle relaxation gait data (as shown in FIG. 2d). The "muscle relaxation state" here means that the user does not need to exert effort during the gait training, and the training unit is driven only by the control unit of the gait training equipment 100, thereby driving the user's feet to swing; The "active force output state" refers to the fact that the user's feet must actively output force during the operation of the training unit.

Figure 2E:
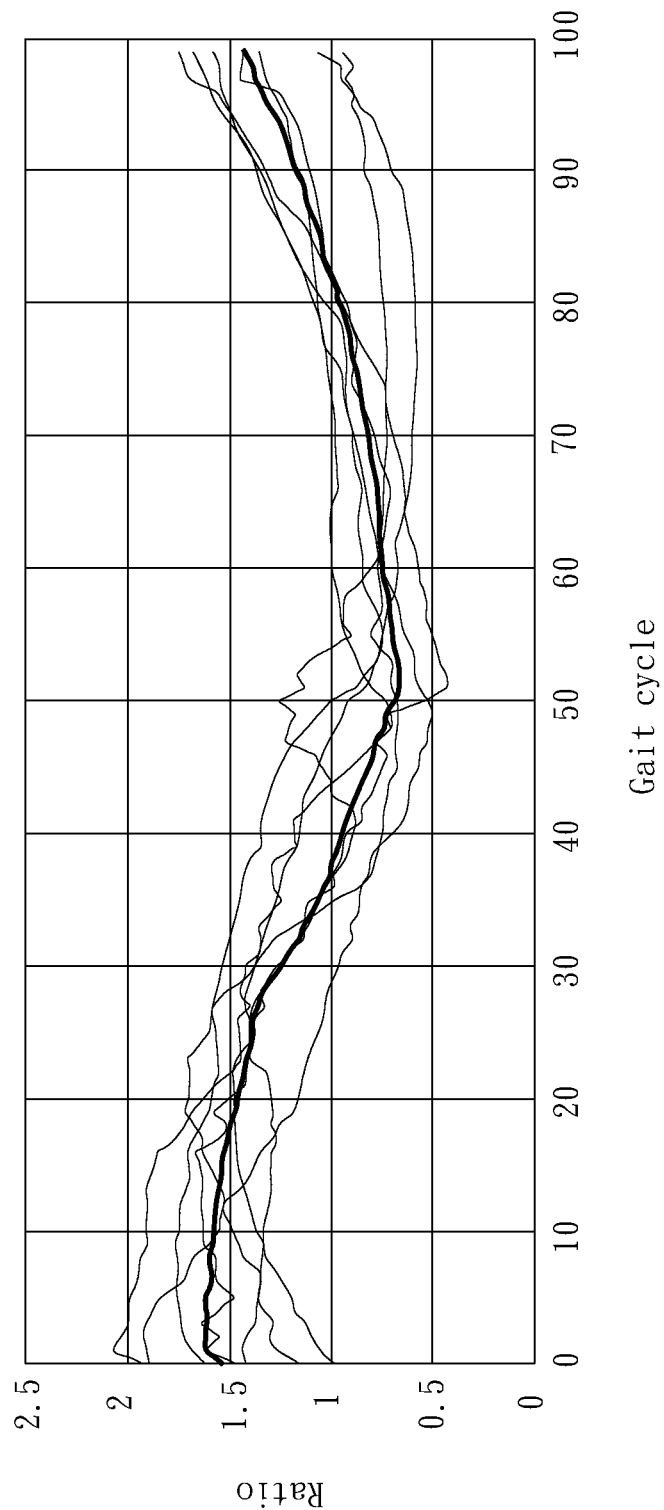
FIG. 2e is a graph of a preferred embodiment of the present invention, showing the ratio and average value of the data measured by a plurality of first users in the state of active force output and muscle relaxation.

In this preferred embodiment, in order to improve the stability of various data, the number of samples taken of the first user is a plurality of samples. According to the ratio of the average value of the gait data of a plurality of the first users' active force output to the average value of the gait data of the muscle relaxation of the muscles of the first users, the standard motion model is then established (as shown in FIG. 2e). In other preferred embodiments, if one of the first users' active output gait data and the first users' muscle relaxation gait data are sufficiently representative, the number of the first users can also be taken as one. Therefore, the number of the first users is not limited only to this preferred embodiment.

Figure 2F:
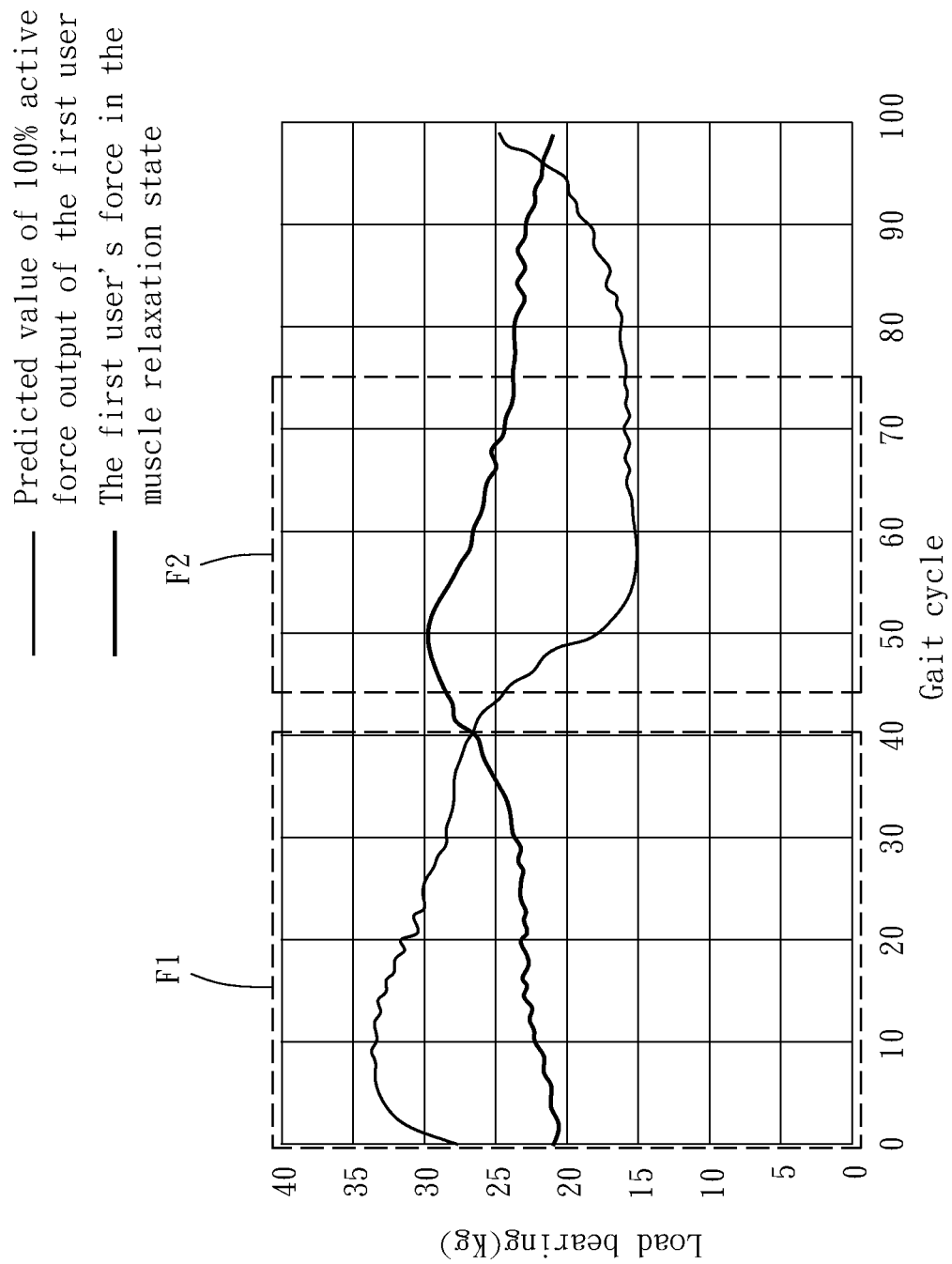
FIG. 2f is a graph of a preferred embodiment of the present invention, showing the center of gravity transfer interval and the hip flexion interval.
Figure 2G:
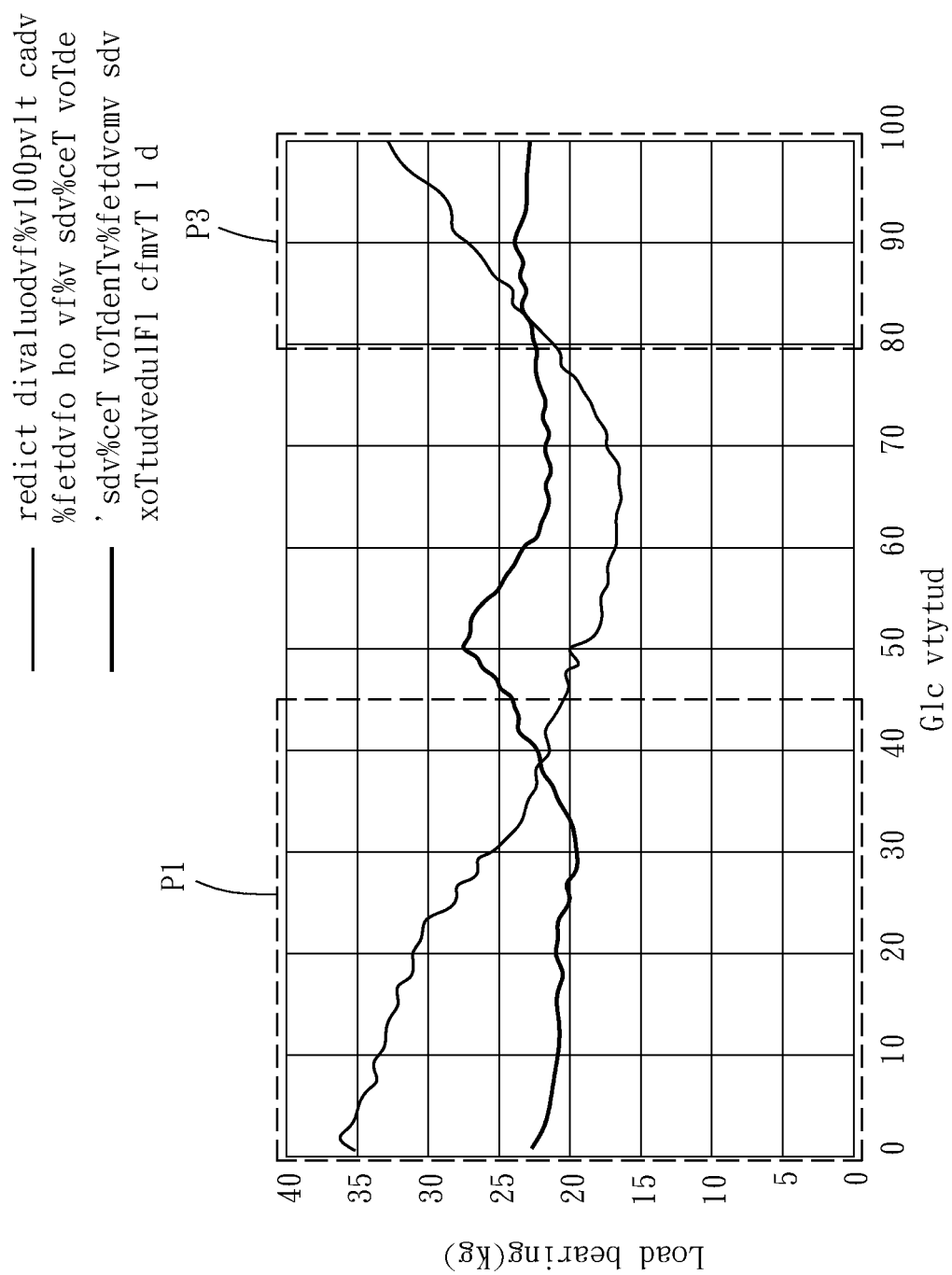
FIG. 2g is a graph of a preferred embodiment of the present invention, showing the center of gravity transfer interval and the knee extension interval.

In this preferred embodiment, as shown in FIGS. 2a, 2f and 2g, the gait cycle is mainly divided into a center of gravity transfer interval F1, a hip flexion interval F2 and a knee extension interval F3. The center of gravity transfer interval F1 is located in the 0-40 equal parts of the gait cycle, the hip flexion interval F2 is located in the 45-70 equal parts of the gait cycle, and the knee extension interval F3 is located in the 80-99 equal parts of the gait cycle.

Taking the right foot of the first user as an example (the judgment method of the left foot is also the same, and will not be repeated here), as shown in FIG. 2f, when located in the center of gravity transfer interval F1, the value sensed by the first user's right foot stepping on the right foot force sensor 102 is greater than a model threshold (the first user's 100% active force output prediction value), when in the hip flexion interval F2, the value sensed by the right foot stepping on the right foot force sensor 102 is less than the model threshold, as shown in FIG. 2g, when in the knee extension interval F3, the right knee pressure sensor 104 is less than the model threshold.

Figure 2H:
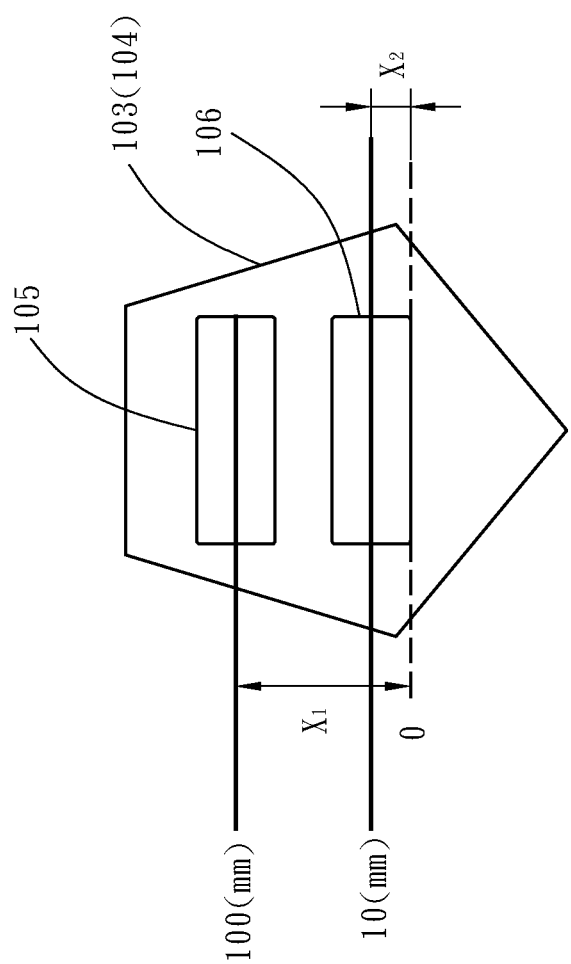
FIG. 2h is a schematic diagram of a preferred embodiment of the present invention, showing the implementation state of the upper sensing element and the lower sensing element of the knee pressure sensor.

In this preferred embodiment, as shown in FIG. 2h, the left knee pressure sensor 103 and the right knee pressure sensor 104 respectively have an upper sensing element 105 and a lower sensing element 106 (because the upper and lower sensing elements 105 and 106 of the left and right knee pressure sensors 103 and 104 and are the same elements and have the same configuration relationship, only one diagram is used, as a schematic diagram of the left knee pressure sensor 103 and the right knee pressure sensor 104). Assuming that the pressure value measured by the upper sensing element 105 is $P_{K1}$, the pressure value measured by the lower sensing element 106 is $P_{K2}$, the shortest distance between the center point of the upper sensing element 105 and the lower end face of the lower sensing element 106 is $X_2$ (in this embodiment 100 mm), then the pressure center position of the left knee pressure sensor 103 (or the right knee pressure sensor $$104) = \frac{X_1 \times P_{K1} + X_2 \times P_{K2}}{P_{K1} + P_{K2}}.$$

Figure 3:
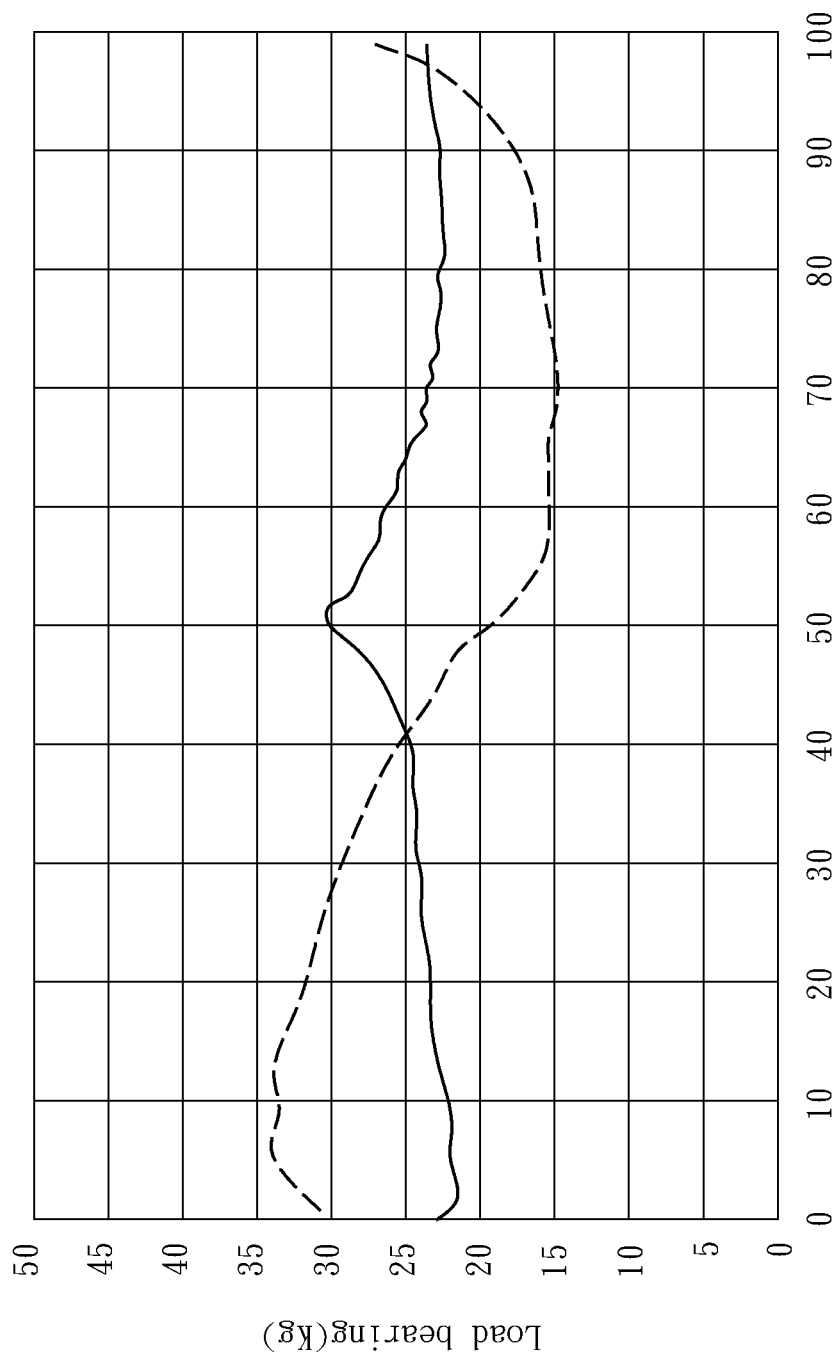
FIG. 3 is a graph of a preferred embodiment of the present invention showing a personalized training model.
Figure 3A:
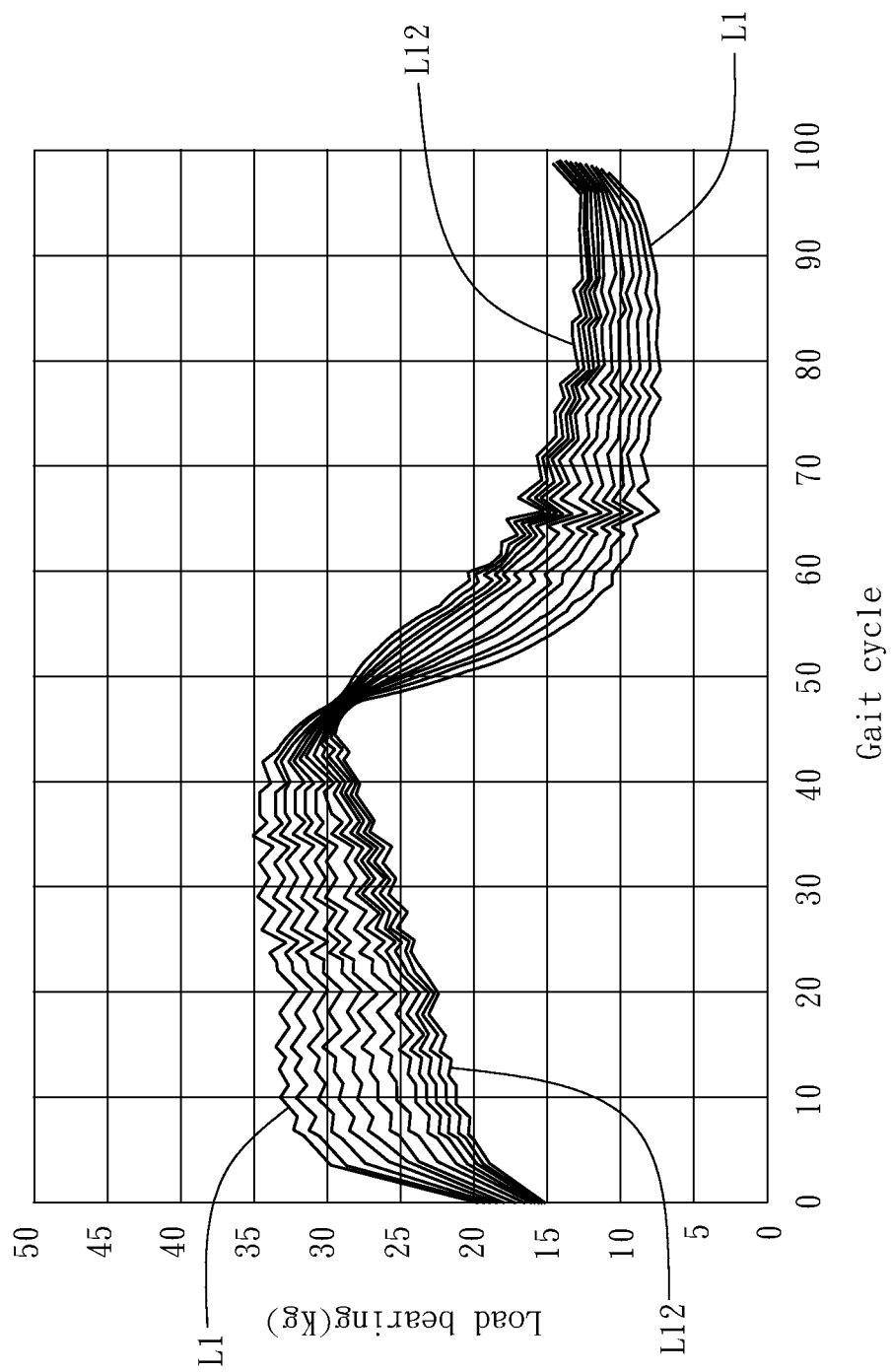
FIG. 3a is a graph of a preferred embodiment of the present invention showing a plurality of personalized training models.

As shown in FIGS. 1 and 3, in step (b), the control unit obtains a motion model of a second user. The second user motion model comprises a second user's muscle relaxation gait data measured during the gait training under the muscle relaxation state of the second user. By combining the second user's muscle relaxation gait data with the standard motion model, a personalized training model is estimated (see FIG. 3). In this preferred embodiment, as shown in FIG. 3*a*, 10%, 15%, 20%, 25%, 30%, 40%, 50%, 60%, 70%, 80%, 90%, and 100% difficulty curves are estimated with the personalized training model (only the 100% difficulty curve L1 and the 10% difficulty curve L12 are indicated in FIG. 3*a*). In this way, the personalized training models with different difficulties are established, and the difficulty curves can be adjusted according to requirements, so the difficulty curves are not limited to this preferred embodiment.

For the right foot, since the center of gravity transfer interval F1 is the stage where the right foot is stepping down, the higher the value measured by the right foot force sensor 102, the higher the difficulty of the personalized training model. When the value measured by the right foot force sensor 102 is lower, it means that the difficulty of the personalized training model is lower. Therefore, between about the gait cycle 0-40, the uppermost curve is the 100% difficulty curve L1, and the lowermost curve is the 10% difficulty curve L12. In the hip flexion interval F2 and the knee extension interval F3 they are the stages of lifting the right foot. Therefore, when the value measured by the right foot force sensor 102 is lower, it means that the difficulty of the personalized training model is higher, and when the value measured by the right foot force sensor 102 is higher, it means that the difficulty of the personalized training model is lower. Therefore, between about the gait cycle 45-100, the lowermost curve is the 100% difficulty curve L1, and the uppermost curve is the 10% difficulty curve L12.

Figure 3B:
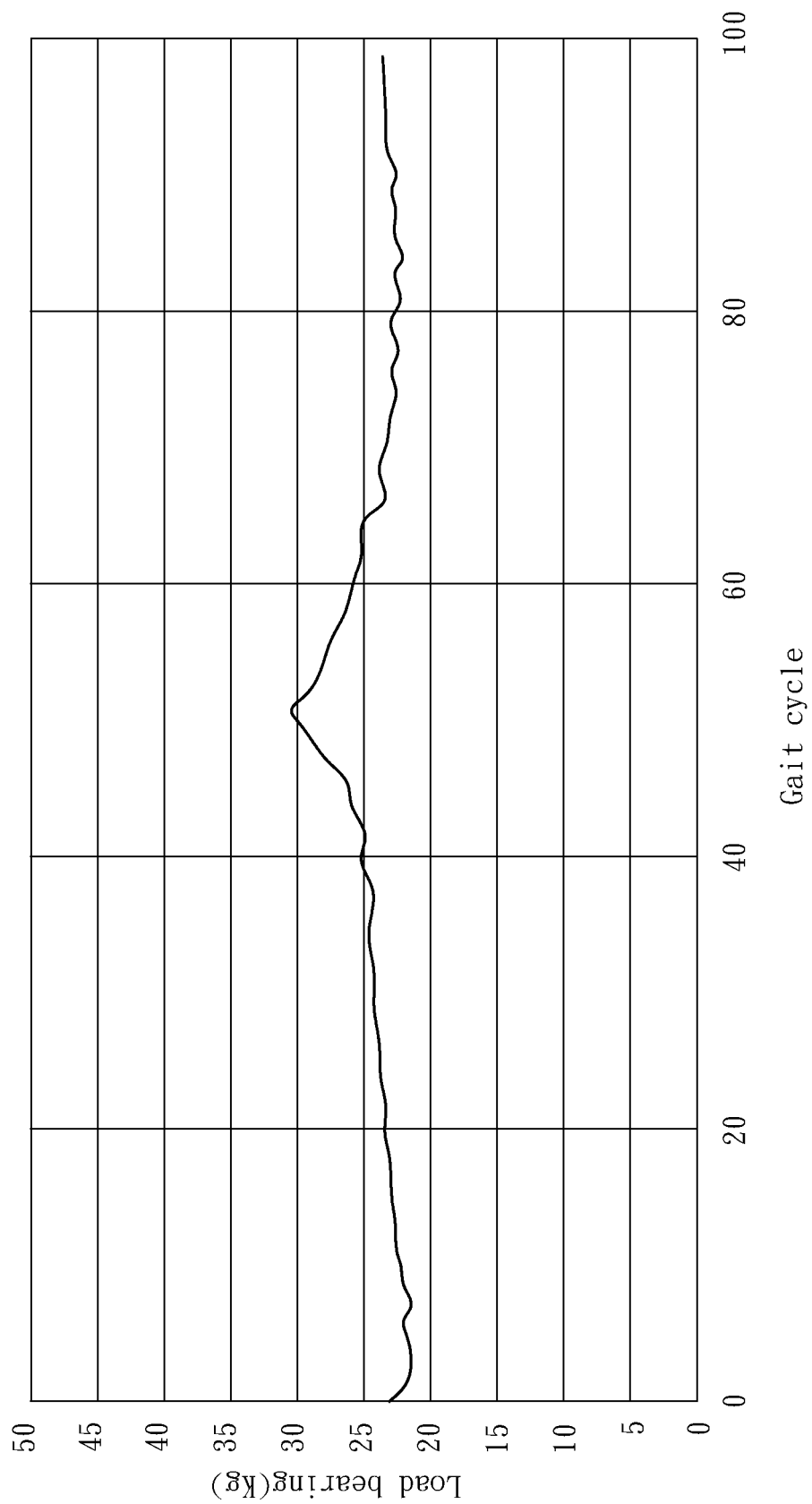
FIG. 3b is a graph of a preferred embodiment of the present invention, showing the data of the muscle relaxation state of the second user.
Figure 3C:
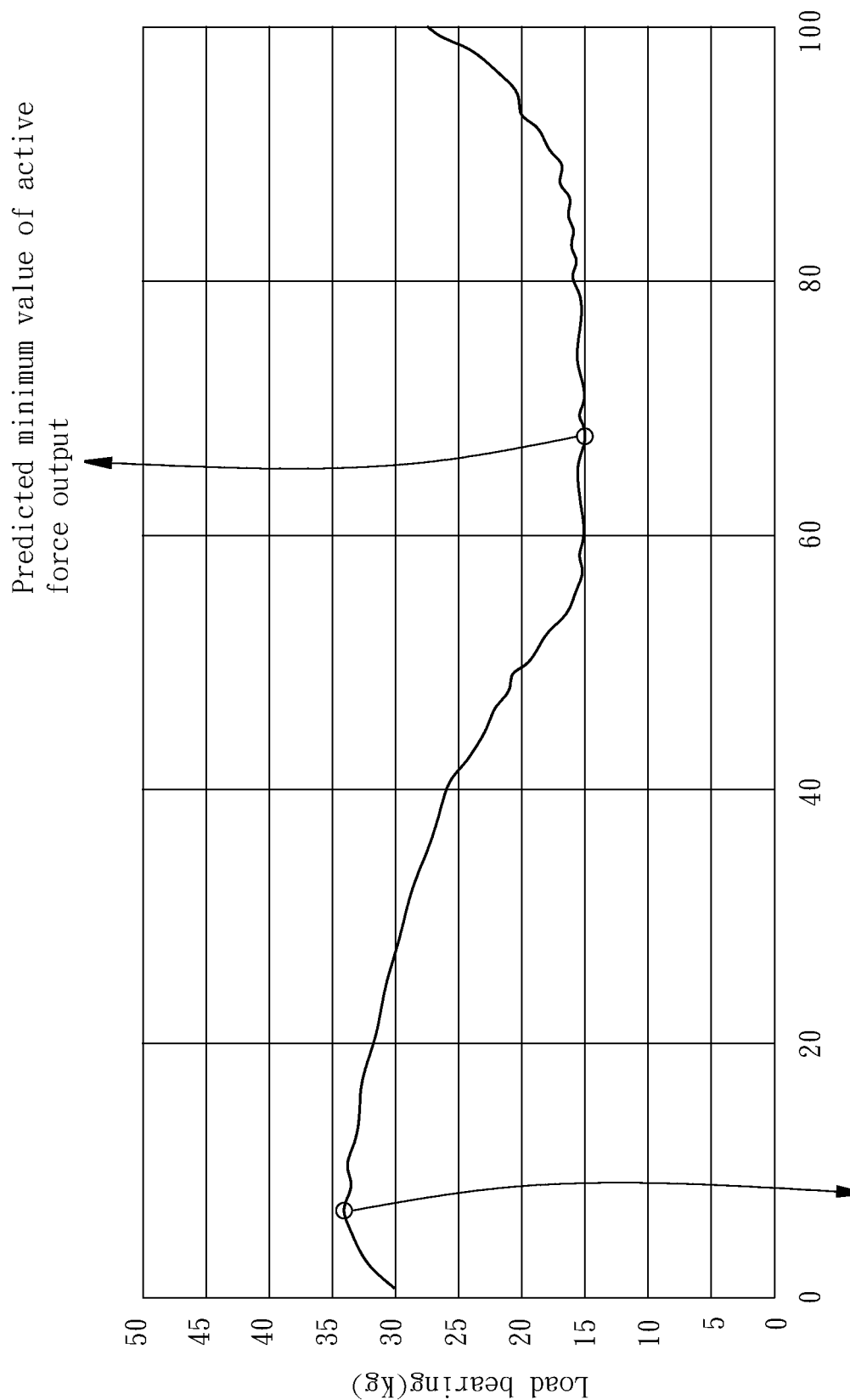
FIG. 3c is a graph of a preferred embodiment of the present invention, showing the predicted maximum value of active force output and the predicted minimum value of active force output in the personalized training model of the second user.
Figure 3D:
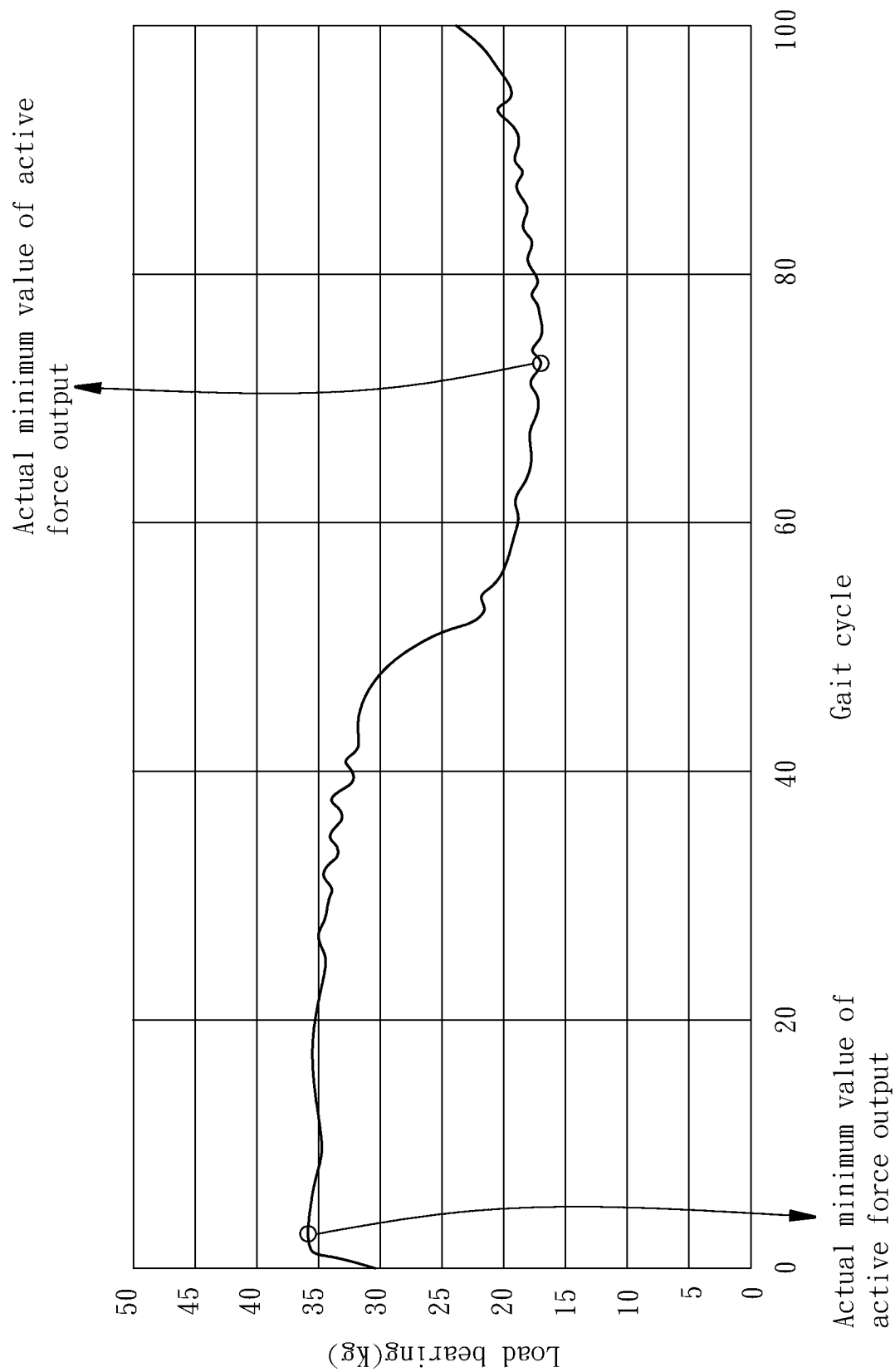
FIG. 3d is a graph of a preferred embodiment of the present invention, showing the actual maximum value of active force output and the actual minimum value of active force output in the actual training state of the second user.
Figure 3E:
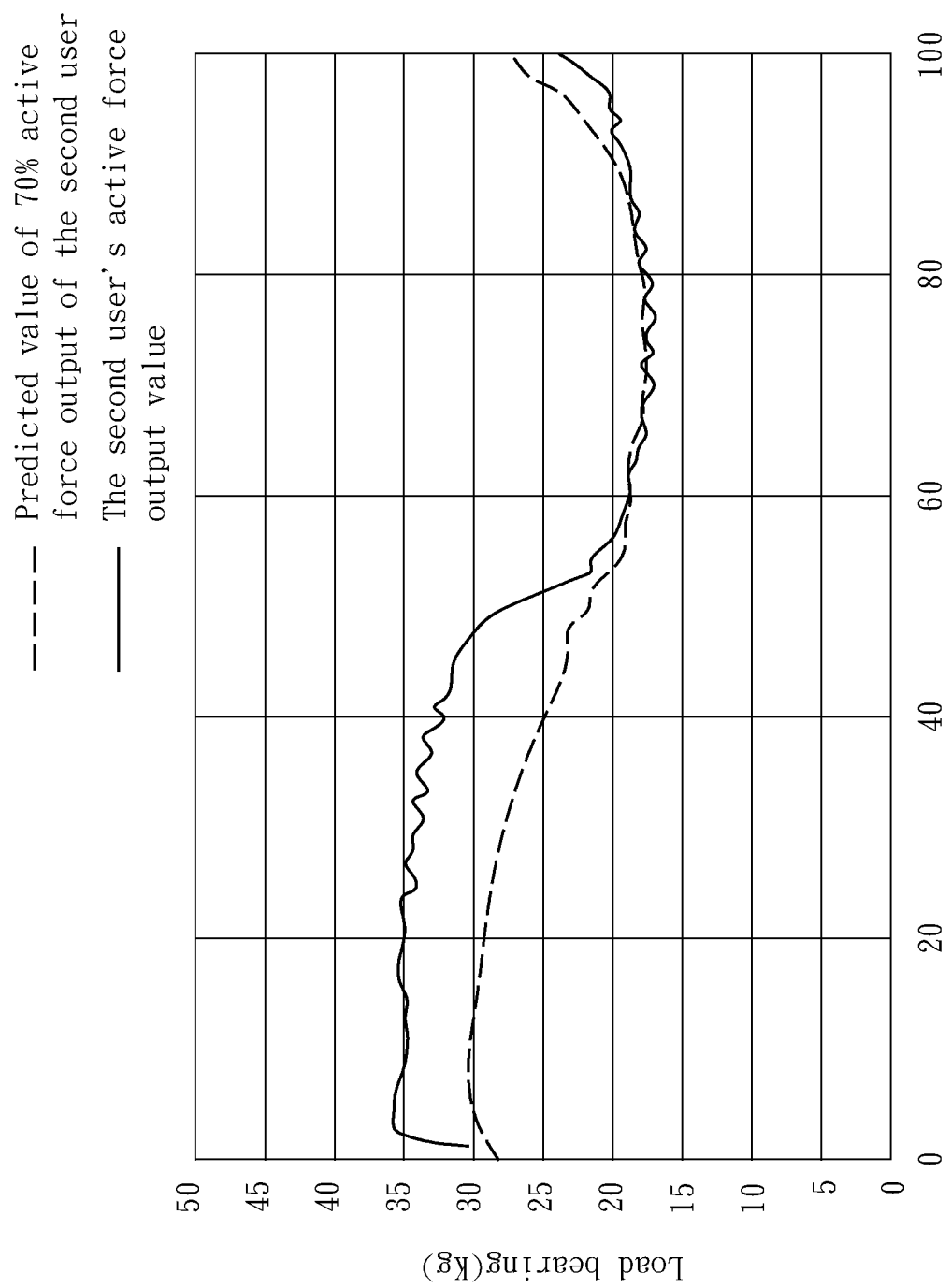
FIG. 3e is a graph of a preferred embodiment of the present invention, showing an auxiliary training model obtained after adjusting the personalized training model.

In this preferred embodiment, as shown in FIGS. 3*b*, 3*c*, 3*d*, and 3*e*, the ways of estimating the personalized training model most suitable for the second user from the personalized training models of different difficulties, first, the second user is in a state of muscle relaxation, taking the right foot as an example, from the value obtained by the right foot force sensor 102, when the second user is in the muscle relaxation state, a maximum value of a muscle relaxation state and a minimum value of a muscle relaxation state in the gait cycle are obtained (as shown in FIG. 3*b*). Then, a predicted maximum value of active force output and a predicted minimum value of active force output in the gait cycle of the second user when the second user is actively outputting force are estimated by the standard motion model (as shown in FIG. 3*c*). Then, using the value obtained by the right foot force sensor 102 under the state of active force output of the second user, when the second user is actively outputting force, an actual maximum value of active force output and an actual minimum value of active force output in the gait cycle are obtained (as shown in FIG. 3*d*). Bring the actual maximum value of active force output, the predicted maximum value of active force output and the maximum value of force in the muscle relaxation respectively into a center of gravity transfer interval calculation formula, and bring the actual minimum value of active force output, the predicted minimum value of active force output and the minimum value of force in the muscle relaxation state respectively into a hip flexion interval calculation formula to get the force output level of the center of gravity transfer interval and the hip flexion interval. Then the suitable personalized training model is recommended by the lower force output level (as shown in FIG. 3*e*). The specific calculation method is as follows:

The center of gravity transfer interval calculation formula:

actual maximum value of active force output−maximum value of force in the muscle relaxation state/predicted maximum value of active force output−muscle relaxation state maximum value=the output level of the center of gravity transfer interval $F1$.

In this preferred embodiment, as shown in FIGS. 3*c* and 3*d*, the output level of the second user in the center of gravity transfer interval $$F1 = \frac{35.651(\text{kg}) - 22.066(\text{kg})}{34.263(\text{kg}) - 22.066(\text{kg})} = 111.37\%.$$

The hip flexion interval calculation formula:

actual minimum value of active force output−minimum value of force in the muscle relaxation state/predicted minimum value of active force output−minimum value of force in the muscle relaxation state=the force output level of the hip flexion interval $F2$.

In this preferred embodiment, as shown in FIGS. 3*c* and 3*d*, the output level of the second user in the hip flexion interval $$F2 = \frac{16.885(\text{kg}) - 23.68(\text{kg})}{15.128(\text{kg}) - 23.68(\text{kg})} = 79.45\%.$$

Since the force output level of the hip flexion interval F2 is smaller than the force output level of the center of gravity transfer interval F1, choose the suitable personalized training mode recommended by the force output level of the hip flexion interval F2, for example, take the model represented by the 80% difficulty curve in FIG. 3*a* as the personalized training model.

As shown in FIGS. 1, 3*c*, 3*d*, 3*e*, and 4, in step (c), the control unit determines whether the actual training state of the user conforms to the standard of the personalized training model, and then adjusts the personalized training model and provides an auxiliary training model.

In this preferred embodiment, the control unit determines whether the actual training state of the second user conforms to the standard of the personalized training model, including a continuous determination way within a specific interval and a single-point trigger determination way within the specific interval. The continuous determination way within the specific interval is to continuously determine whether the actual training state of the second user conforms to the standard of the personalized training model in one of the intervals of the gait cycle (for example: the center of gravity transfer interval F1, the hip flexion interval F2, the knee extension interval F3). When the second user meets the standard at the beginning of training, the training unit of the gait training equipment 100 maintains the originally set speed. When it does not meet the standard, the control unit controls the training unit to reduce the running speed (in this preferred embodiment, the running speed is set to be reduced by 12% each time, and the minimum speed is reduced to 25% of the original set speed, but not limited to this). When the second user meets the standard after the speed of the training unit is reduced, the control unit controls the running speed of the training unit to increase by 38% each time until the 100% of the original set speed is reached. The single-point trigger determination way is that any data in one of the intervals of the gait cycle (for example: the center of gravity transfer interval F1, the hip flexion interval F2, the knee extension interval F3) meets the standard of the personalized training model, and it is deemed to meet the standard of the personalized training model, so as to avoid the second user needing continuous force output to adjust the personalized training model.

In this preferred embodiment, one of the methods for the control unit to determine whether the second user reaches hip flexion in the hip flexion interval F2 is, taking the right foot as an example, to determine by combining with the parameters of the position of the pressure center $X_K$ measured by the right knee pressure sensor 104 when the second user is in the active force output state, the average pressure center position $\overline{X_K}$ measured by the second user in the relaxed state, the force $P_F$ of the second user in the active force output state sensed by the right foot force sensor 102, the force $U_{FR}$ of the second user in a relaxed state sensed by the right foot force sensor 102, personalized training model $U_{FP}$ and the set difficulty R %. When judging that the second user has reached hip flexion at the hip flexion interval F2, the following conditions must be met: $(X_K > \overline{X_K} + R \% \times U_{RKX}) \cap (P_F < (U_{FP} - U_{FR}) \times R \% + U_{FP})$, wherein the variation range $U_{RKX}$ of the pressure center of the second user in the relaxed state is half of the difference between the maximum value and the minimum value of the pressure center position recorded by the hip flexion interval F2 of the second user in the relaxed state, the average pressure center position $\overline{X_K}$ is the average value of the pressure center position recorded by the hip flexion interval F2.

In this preferred embodiment, one of the methods for the control unit to determine whether the second user reaches knee extension in the knee extension interval F3 is, taking the right foot as an example, to determine by combining with the parameters of the pressure value $P_K$ measured by the right knee pressure sensor 104 of the second user in the active force output state, the pressure value $U_{RKP}$ measured by the right knee pressure sensor 104 of the second user when the muscles are relaxed and the set difficulty R %. When judging that the second user has reached the knee extension action at the knee extension interval F3, the following conditions must be met: $P_K < 0.9 - 0.4 \times R \% \times U_{RKP}$.

In this preferred embodiment, judging whether the actual training state of the second user meets the standard of the personalized training model by means of the continuous determination way within the interval is based on whether the measurement data of the second user in the hip flexion interval F2 reaches 80% of the predicted value of the personalized training model. If it does not reach 80% of the predicted value of the personalized training model, it is regarded as not meeting the standard. If only 50% of the predicted value of the personalized training model is reached, it is only regarded as participating in the gait training. In addition, in the personalized training model, when the second user undergoes five gait cycles of gait training, if four of them meet the standard of the personalized training model, the control unit will provide the auxiliary training model by increasing the difficulty of the personalized training model. After the second user has undergone the gait training of the gait cycle for five times, if four of them do not meet the standard of the personalized training model, the control unit will provide the auxiliary training model by reducing the difficulty of the personalized training model.

In this preferred embodiment, as shown in FIG. 3e, the 70% difficulty of the personalized training model is taken as the auxiliary training model as an example. In other preferred embodiments, the personalized training model is judged and adjusted by means of the continuous determination way within the specific interval. According to the personalized training model, 10%, 15%, 20%, 25%, 30%, 40%, 50%, 60%, 80%, 90%, 100% difficulty can be defined as the auxiliary training model. Judging and adjusting the personalized training model by means of the single-point trigger determination way within the specific interval, 20%, 40%, 60%, 80%, 100% of the difficulty can be defined as the auxiliary training model according to the personalized training model.

Thereby, a personalized motion model belonging to the second user according to the state of the second user can be planned by a method for real-time adjustment of gait training parameter 10 provided by the present invention, and in the training, suitable auxiliary training models according to the data of the second user's output can be recommended, so as to achieve the effect of adjusting the training difficulty in real time according to the actual performance during training.

The above-mentioned preferred embodiments are intended to help understand the principles and methods of the present invention, and the present invention is not limited to the above-mentioned preferred embodiments. Any combinations and modifications within the spirit and principle of the present invention shall fall within the protection scope of the present invention.

What is claimed is:

1. A method for real-time adjustment of gait training parameter applicable to a gait training equipment, said gait training equipment comprising a sensing unit, a training unit and a control unit, said control unit being electrically connected to said sensing unit and said training unit and controlling the operation of said training unit, said method for real-time adjustment of gait training parameter comprising the steps of:
 (a) said sensing unit collects a muscle relaxation gait data of at least one first user measured during gait training in a muscle relaxation state and an active force output gait data of said at least one first user measured during the gait training in the first user's active force output state, and then said control unit establishes a standard motion model based on the ratio of the first user's active force output gait data to the first user's muscle relaxation gait data;
 (b) said control unit obtains a motion model of a second user, which comprises the muscle relaxation gait data of the second user measured during the gait training under the muscle relaxation state of the second user, then estimate at least one personalized training model by combining the second user's muscle relaxation gait data with said standard motion model; and
 (c) said control unit determines whether an actual training state of the second user conforms to the standard of said at least one personalized training model, and then adjusts said at least one personalized training model and provides an auxiliary training model, and the control unit is configured to control an output of the training unit to move the second user based on the auxiliary training model.

2. The method for real-time adjustment of gait training parameter as claimed in claim 1, wherein said gait training comprises at least one gait cycle, and said gait cycle is divided into a center of gravity transfer interval, a hip flexion interval and a knee extension interval.

3. The method for real-time adjustment of gait training parameter as claimed in claim 1, wherein in said step (b), said at least one personalized training model is plural.

4. The method for real-time adjustment of gait training parameter as claimed in claim 2, wherein in said step (b), the calculation method of said control unit to estimate said personalized training model is, from the muscle relaxation gait data of the second user, when the muscle relaxation state of the second user is obtained, a maximum value of force in a muscle relaxation state and a minimum value of force in a muscle relaxation state in the gait cycle are obtained, then, a predicted maximum value of active force output and a predicted minimum value of active force output in the gait cycle of the second user when the second user is actively outputting force are estimated by the standard motion model, then use the value obtained by the sensing unit when the second user is in the active force output state to obtain an actual maximum value of active force output and an actual minimum value of active force output in the gait cycle when the second user actively outputs force, and respectively bring the actual maximum value of active force output, the predicted maximum value of active force output and the maximum value of force in the muscle relaxation state into a center of gravity transfer interval calculation formula, and respectively bring the actual minimum value of active force output, the predicted minimum value of active force output and the minimum value of force in the muscle relaxation state into a hip flexion interval calculation formula to get the force output level of the center of gravity transfer interval and the force output level of the hip flexion interval, then use the lower force output level as the personalized training model for the second user.

5. The method for real-time adjustment of gait training parameter as claimed in claim 2, wherein said sensing unit comprises two knee pressure sensors and two sole force sensor; in step (c) of the method for real-time adjustment of gait training parameter, when said control unit determines whether the second user reaches hip flexion in the hip flexion interval, the following conditions must be met: $(X_K > \overline{X_K} + R\% \times U_{RKX}) \cap (P_F < (U_{FP} - U_{FR}) \times R\% + U_{FR})$, where $X_K$ is a pressure center position measured by one of said knee pressure sensors when the second user is in the active force output state, $\overline{X_K}$ is an average pressure center position measured by the knee pressure sensor when the second user is in a relaxed state, $U_{FR}$ is a force value measured by one of said sole force sensors when the second user is in a relaxed state, $U_{FP}$ is said personalized training model, R % is a set difficulty.

6. The method for real-time adjustment of gait training parameter as claimed in claim 2, wherein said sensing unit comprises two knee pressure sensors and two sole force sensors, in step (c) of the method for real-time adjustment of gait training parameter, when said control unit determines whether the second user reaches knee extension in the knee extension interval, the following conditions must be met: $P_K < 0.9 - 0.4 \times R\% \times U_{RKP}$, where $P_K$ is a pressure value measured by one of said knee pressure sensors when the second user is in the active force output state, $U_{RKP}$ is a pressure value measured by the one knee pressure sensor of said two knee pressure sensors when the muscle of the second user is relaxed, R % is the set a set difficulty.

7. The method for real-time adjustment of gait training parameter as claimed in claim 1, wherein in step (c), the method of judging whether the actual training state of the second user meets the standard of said personalized training model comprises a continuous determination way within an interval and a single-point trigger determination way within the interval.

8. The method for real-time adjustment of gait training parameter as claimed in claim 1, wherein in step (c), when the actual training state of the second user does not meet the standard of the personalized training model, said control unit provides said auxiliary training model by reducing a difficulty of said personalized training model.

9. The method for real-time adjustment of gait training parameter as claimed in claim 1, wherein in step (c), when the actual training state of the second user has met the standard of said personalized training model, said control unit provides said auxiliary training model by increasing a difficulty of said personalized training model.

* * * * *